(12) United States Patent
Cinader, Jr. et al.

(10) Patent No.: US 8,114,327 B2
(45) Date of Patent: Feb. 14, 2012

(54) ORTHODONTIC INDIRECT BONDING TRAY WITH MOISTURE CONTROL

(75) Inventors: David K. Cinader, Jr., Yorba Linda, CA (US); James D. Cleary, Glendora, CA (US)

(73) Assignee: 3M Innovation Properties Company, St. Paul, MN (US)

( * ) Notice: Subject to any disclaimer, the term of this patent is extended or adjusted under 35 U.S.C. 154(b) by 42 days.

(21) Appl. No.: 12/566,221

(22) Filed: Sep. 24, 2009

(65) Prior Publication Data

US 2010/0015577 A1 Jan. 21, 2010

Related U.S. Application Data

(63) Continuation of application No. 12/048,641, filed on Mar. 14, 2008, now abandoned, which is a continuation of application No. 11/422,614, filed on Jun. 7, 2006, now Pat. No. 7,364,428.

(51) Int. Cl.
*B29C 33/40* (2006.01)

(52) U.S. Cl. .................................. 264/219; 264/308

(58) Field of Classification Search .................. 433/2, 3, 433/8, 9, 24, 213; 128/861, 862; 264/16–20, 264/219, 308
See application file for complete search history.

(56) References Cited

U.S. PATENT DOCUMENTS

| | | |
|---|---|---|
| 4,360,341 A | 11/1982 | Dellinger |
| 4,501,554 A | 2/1985 | Hickham |
| 4,551,096 A | 11/1985 | Dellinger |
| 4,657,508 A | 4/1987 | Dellinger |
| 5,059,118 A | 10/1991 | Breads et al. |
| 5,971,754 A | 10/1999 | Sondhi et al. |
| 5,980,249 A | 11/1999 | Fontenot |
| 6,123,544 A | 9/2000 | Cleary |
| 6,126,443 A | 10/2000 | Burgio |
| 6,142,780 A | 11/2000 | Burgio |
| 6,299,440 B1 | 10/2001 | Phan et al. |
| 6,497,575 B2 | 12/2002 | Zavitsanos et al. |
| 6,607,382 B1 | 8/2003 | Kuo et al. |
| 7,020,963 B2 | 4/2006 | Cleary et al. |
| 7,364,428 B2 | 4/2008 | Cinader, Jr. et al. |
| 2002/0081555 A1 | 6/2002 | Wiesel |
| 2004/0209218 A1 | 10/2004 | Chishti et al. |
| 2004/0219471 A1 | 11/2004 | Cleary et al. |
| 2004/0219473 A1 | 11/2004 | Cleary et al. |

(Continued)

FOREIGN PATENT DOCUMENTS

KR 355842 10/2002

*Primary Examiner* — Sunil K Singh
(74) *Attorney, Agent, or Firm* — James D. Christoff; Kevin W. Weber

(57) ABSTRACT

An indirect bonding apparatus for orthodontic bonding procedures includes a tray having inner wall sections defining a channel for receiving the patient's dental arch. A number of orthodontic appliances are detachably connected to the tray along the channel, and each appliance includes a base for bonding the appliance to the tooth. The wall sections include at least one groove extending along the base of at least one appliance in order to provide a space between the wall sections and the patient's tooth structure when the tray is received on the patient's dental arch. The space hinders the flow of oral fluids such as saliva in directions toward the base in order to help ensure that the fluids do not adversely affect the strength of the resulting adhesive bond between the appliance and the tooth.

10 Claims, 3 Drawing Sheets

U.S. PATENT DOCUMENTS

| | | |
|---|---|---|
| 2004/0253562 A1 | 12/2004 | Knopp |
| 2005/0074716 A1 | 4/2005 | Cleary et al. |
| 2005/0133384 A1 | 6/2005 | Cinader et al. |
| 2005/0136370 A1 | 6/2005 | Brennan et al. |
| 2005/0244790 A1* | 11/2005 | Kuperman .................... 433/213 |
| 2005/0277084 A1 | 12/2005 | Cinader et al. |
| 2006/0029908 A1 | 2/2006 | Allred et al. |
| 2006/0223021 A1 | 10/2006 | Cinader, Jr. et al. |
| 2006/0223031 A1 | 10/2006 | Cinader, Jr. et al. |
| 2006/0257821 A1 | 11/2006 | Cinader, Jr. et al. |
| 2007/0238066 A1* | 10/2007 | Kopelman et al. .............. 433/24 |

* cited by examiner

ORTHODONTIC INDIRECT BONDING TRAY WITH MOISTURE CONTROL

CROSS-REFERENCE TO RELATED APPLICATIONS

This application is a continuation of U.S. patent application Ser. No. 12/048,641, filed Mar. 14, 2008 now abandoned which is a continuation of U.S. patent application Ser. No. 11/422,614, filed Jun. 7, 2006, issued as U.S. Pat. No. 7,364,428.

BACKGROUND OF THE INVENTION

1. Field of the Invention

This invention broadly relates to orthodontic indirect bonding apparatus that is useful for affixing orthodontic appliances to a patient's teeth. More particularly, the present invention is directed towards orthodontic indirect bonding apparatus with structure for controlling moisture in the oral cavity such as saliva during a bonding procedure.

2. Description of the Related Art

Orthodontic treatment involves movement of malpositioned teeth to desired locations in the oral cavity. Orthodontic treatment can improve the patient's facial appearance, especially in instances where the teeth are noticeably crooked or where the jaws are out of alignment with each other. Orthodontic treatment can also enhance the function of the teeth by providing better occlusion during mastication.

One common type of orthodontic treatment involves the use of tiny, slotted appliances known as brackets. The brackets are fixed to the patient's teeth and an archwire is placed in the slot of each bracket. The archwire forms a track to guide movement of teeth to desired locations.

The ends of orthodontic archwires are often connected to small appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly referred to collectively as "braces".

In general, orthodontic appliances that are adapted to be adhesively bonded to the patient's teeth are placed and connected to the teeth by either one of two procedures: A direct bonding procedure, or an indirect bonding procedure. In the direct bonding procedure, the appliance is grasped with a pair of tweezers or other hand instrument and placed by the practitioner on the surface of the tooth in its desired location, using a quantity of adhesive to fix the appliance to the tooth. In the indirect bonding procedure, a transfer tray is constructed with wall sections having a shape that matches the configuration of at least part of the patient's dental arch, and appliances such as orthodontic brackets are releasably connected to the tray at certain, predetermined locations. After an adhesive is applied to the base of each appliance, the tray is placed over the patient's teeth and remains in place until such time as the adhesive has hardened. Next, the tray is detached from the teeth as well as from the appliances, with the result that all of the appliances previously connected to the tray are now bonded to the respective teeth at their intended, predetermined locations.

Indirect bonding techniques offer a number of advantages over direct bonding techniques. For example, it is possible with indirect bonding techniques to bond a plurality of appliances to a patient's dental arch simultaneously, thereby avoiding the need to bond each appliance in individual fashion. In addition, the transfer tray helps to locate the appliances in their proper, intended positions such that adjustment of each appliance on the surface of the tooth before bonding is avoided. The increased placement accuracy of the appliances that is often afforded by indirect bonding procedures helps ensure that the patient's teeth are moved to their proper, intended positions at the conclusion of treatment.

The control of moisture during a bonding procedure is often deemed important, since the presence of moisture can adversely affect the resultant bond strength between the appliance and the tooth. If, for example, the appliance inadvertently detaches from the tooth during the course of treatment, the patient must often return to the practitioner's office for rebonding of the appliance or replacement of the appliance before full treatment can resume. Obviously, unintentional debonding of orthodontic appliances is a nuisance to both the practitioner and to the patient that is best avoided if at all possible.

In the past, a variety of methods were used to reduce the presence of moisture in the patient's oral cavity during orthodontic bonding procedures. For example, some practitioners use absorbent articles such as cotton rolls to absorb saliva and/or blood along with cheek retractors to help keep the mouth tissue in an open, stationary position. Other practitioners use suction devices such as Nola brand dry field cheek retractors that have suction tubing for drawing fluids out of the oral cavity. Other practitioners have proposed the use of an anti-sialagogue, a drug that can be used to dry the salivary glands during a bonding procedure.

The control of moisture during an indirect bonding procedure is often considered more challenging than controlling moisture during a direct bonding procedure. For one thing, in an indirect bonding procedure, it is important to simultaneously keep multiple bond sites dry. In addition, many indirect bonding trays have interior wall sections that closely fit the patient's teeth, and consequently tend to spread moisture over relatively large portions of the tooth surface as the tray is placed onto the dental arch.

SUMMARY OF THE INVENTION

The present invention relates to improved indirect bonding apparatus that has structure for controlling moisture such as saliva during a bonding procedure. In particular, the present invention concerns an indirect bonding apparatus that includes a tray having structure that functions as a moat to help confine or at least hinder the passage of moisture in directions toward the orthodontic bonding adhesive while the adhesive is curing. As a result, the probability of a compromised adhesive bond and subsequent inadvertent detachment of the appliances during the course of treatment due to bond failure is reduced.

In more detail, the present invention in one aspect is directed toward an apparatus for indirect bonding of orthodontic appliances. The apparatus includes a tray having wall sections defining a channel for receiving a patient's dental arch. The wall sections have a configuration that matches portions of the patient's dental arch. The apparatus further includes a number of orthodontic appliances detachably connected to the tray, and each appliance includes a base for bonding the appliance to a tooth. The wall sections surround the appliances and include at least one groove extending along the base of at least one appliance in order to provide a space between the wall sections and the patient's tooth structure when the tray is received on the patient's dental arch.

Another aspect of the invention is directed toward a method for controlling moisture during indirect orthodontic bonding procedures. The method comprises:

providing an indirect bonding tray having wall sections defining an elongated channel;

detachably connecting a number of orthodontic appliances to the tray along the channel such that the wall sections surround the appliances;

applying a quantity of adhesive to the base of each appliance;

placing the channel of the tray over the patient's dental arch such that the adhesive of each appliance contacts the patient's teeth; and maintaining a space between the wall sections and the patient's teeth in a region next to the base of the appliances during at least a portion of the time that the adhesive contacts the patient's teeth in order to hinder the movement of moisture in a direction toward the adhesive.

These and other aspects of the invention are described in more detail in the paragraphs that follow and are illustrated in the accompanying drawings.

DEFINITIONS

Figure 1:
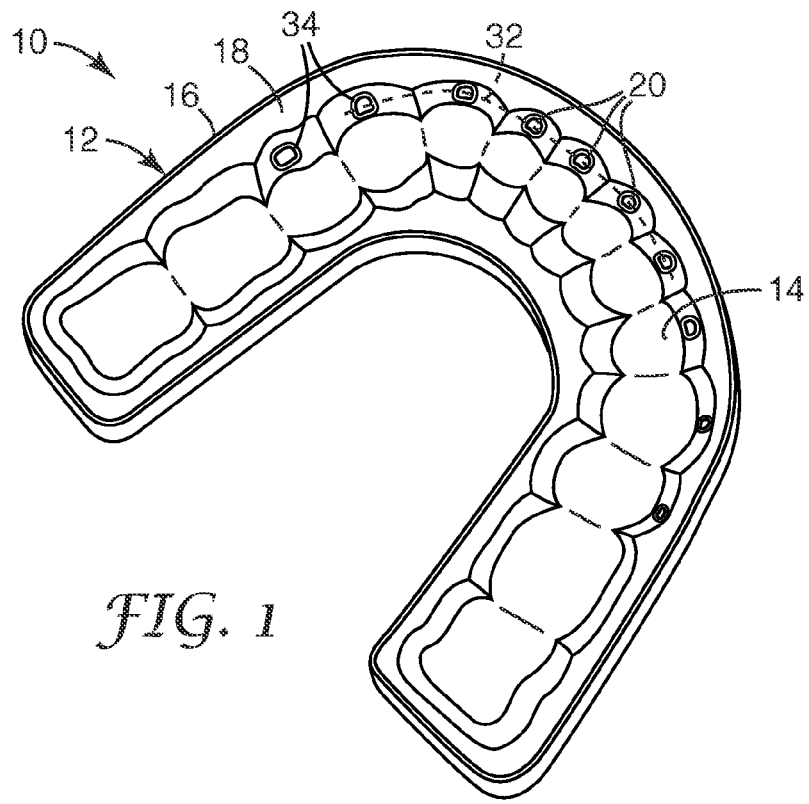
FIG. 1 is a perspective view of an orthodontic indirect bonding apparatus that is constructed in accordance with one embodiment of the invention.

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's cheeks or lips.

DETAILED DESCRIPTION OF THE PREFERRED EMBODIMENTS

An apparatus for indirect bonding of orthodontic appliances according to one embodiment of the invention is illustrated in FIGS. 1-4 and is broadly designated by the numeral 10. The apparatus 10 includes a tray 12 having a channel 14 for receiving a patient's dental arch. In the exemplary tray 12 shown in the drawings, the channel 14 is adapted to receive a patient's lower dental arch, although it should be understood in this regard that as an alternative the tray 12 may be constructed to receive the patient's upper dental arch.

The tray 12 may be constructed according to any one of a variety of known techniques. In the example shown in FIGS. 1-4, the tray 12 includes an outer shell 16 that is relatively stiff and an inner section of matrix material 18 that is relatively flexible. A suitable material for the shell 16 is a sheet of polycarbonate such as Makrolon brand material from Bayer or Lexan brand polycarbonate from GE having a thickness of 0.06 in. (1.5 mm). Other materials, such as polyethyleneterephthalate ("PET"), polyethyleneterephthalate glycol ("PETG") or polystyrene may also be used.

Preferably, the matrix material 18 has a relatively low viscosity before hardening so that intimate contact between the matrix material 18 and orthodontic appliances received in the channel 14 is assured. In this manner, the matrix material 18 is able to substantially penetrate in various recesses, cavities and other structural features of each appliance so that a secure connection between the appliance and the matrix material 18 can be established. An example of a suitable matrix material having a relatively low viscosity before curing is a silicone material such as "RTV615" silicone material from General Electric.

The matrix material 18 preferably has a viscosity before curing that is less than about 60,000 cp. More preferably, the matrix material 18 has a viscosity before curing that is less than about 25,000 cp. Most preferably, the matrix material has a viscosity that is less than about 8,000 cp. Once hardened, the matrix material 18 has a Shore A hardness that is in the range of about 10 to about 80, more preferably in the range of about 30 to about 60 and most preferably in the range of about 40 to about 50.

Alternatively, the matrix material 18 may comprise a dental impression material or a bite registration material. Suitable materials include polyvinylsiloxane impression material, such as Memosil 2 brand vinyl polysiloxane material from Heraeus Kulzer Inc., or Peppermint Snap brand clear bite registration material from Discus Dental. Another suitable matrix material is Affinity Crystal brand silicone impression material from Clinician's Choice Dental Products, Inc. If a light-curable adhesive is to be subsequently used for bonding the appliances to the patient's teeth, the matrix material 18 is preferably optically clear and transmits actinic radiation without substantial absorption once hardened.

Preferably, the inner wall sections of the matrix material 18 that face the channel 14 have contours that precisely match the contours of the individual teeth of the patient, as well as an overall configuration that matches the orientation of each tooth relative to other teeth in the same dental arch when the teeth are in their initial maloccluded condition at the beginning of treatment. As a result, when the tray 12 is placed over the patient's dental arch, the channel 14 of the tray 12 provides a mating fit with the patient's teeth such that little, if any, tolerance or "slop" is present and relative movement between the tray and the dental arch is substantially hindered.

Figure 2:
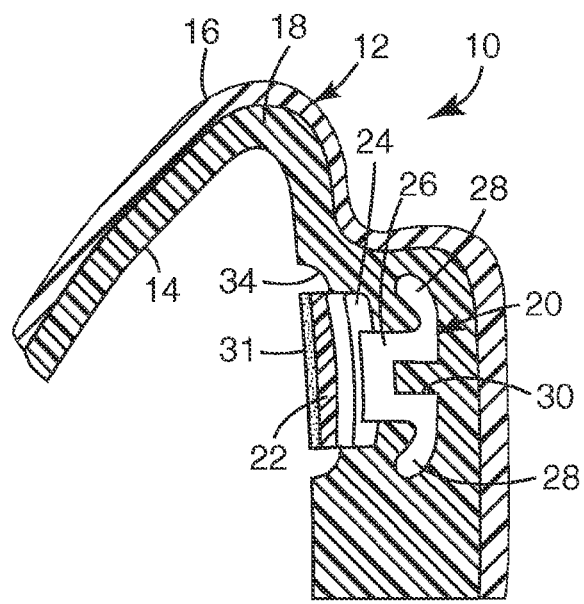
FIG. 2 is an enlarged side cross-sectional view of the apparatus depicted in FIG. 1.
Figure 3:
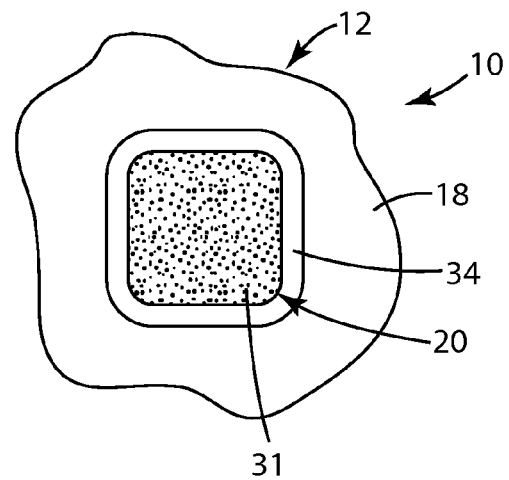
FIG. 3 is a fragmentary elevational view of a portion of the apparatus shown in FIGS. 1 and 2 looking toward the base of an appliance located within a channel of the apparatus.
Figure 4:
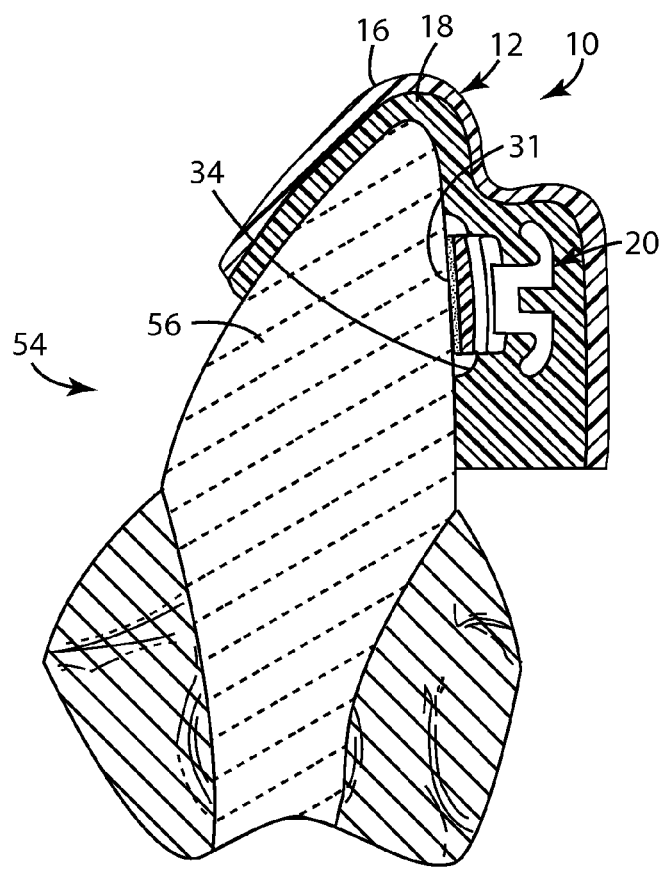
FIG. 4 is a side cross-sectional view in somewhat smaller scale illustrating the apparatus of FIGS. 1-3 as it appears when placed over the teeth of a dental arch.

The apparatus 10 also includes a number of orthodontic appliances 20 that are detachably connected to the tray 12. In FIGS. 2-4, the exemplary illustrated orthodontic appliance 20 is an orthodontic bracket, although other appliances are also possible. Examples of other suitable appliances include buccal tubes, buttons, formed "bumps" made, e.g., of composite material, or any other metal or non-metal "handle" or other structure connected to the teeth that provides an attachment point for a force member such as a wire, aligner tray, polymeric strip, elastomeric band or chain, or any combination of the foregoing. If desired, appliances may be omitted for some of the teeth in the dental arch such as molar teeth or teeth that have only partially erupted.

The exemplary appliance 20 as shown in FIGS. 2-4 includes a base 22 (FIG. 2) that is connected to a base flange 24. The appliance 20 also has a body 26 that extends outwardly from the base flange 24. A pair of tiewings 28 is connected to the body 26, and an archwire slot 30 extends through a space between the tiewings 28.

The base flange 24, the body 26 and the tiewings 28 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina) and plastic materials (such as fiber-reinforced polycarbonate). Optionally, the base flange 24, the body 26 and the tiewings 28 are integrally made as a unitary component.

The base 22 of the appliance 20 is preferably made of a material different than the material comprising the base flange 24, and has a configuration that matches the configuration of a portion of a patient's tooth structure. More particularly, the base 22 has a concave contour that is a replica of the convex contour of the portion of the patient's tooth that represents the ultimate desired location of the appliance 20 on the tooth. Optionally, the concave contour of the base 22 is a compound concave contour (i.e., curved in directions along two mutually perpendicular reference planes).

A bonding adhesive 31 extends across the base 22 for securing the appliance 20 to the patient's tooth. The bonding adhesive 31 may be any orthodontic adhesive suitable for use as an indirect bonding adhesive. Optionally, the adhesive 31 is a two-component adhesive, wherein the first component is Transbond brand XT primer and the second component is Transbond brand Plus self-etching primer, both from 3M Unitek. The first component of such two-component adhesive is applied to the base 22 and the second component is applied to the area of each patient's tooth that is to receive the appliance 20.

Another option is to use a preliminary teeth etching step (such as by exposing the teeth to 37% phosphoric acid or equivalent), followed by applying a suitable chemical curing adhesive. Examples of suitable chemical curing adhesives include Sondhi brand Rapid-Set indirect bonding adhesive and Unite brand adhesive, both from 3M Unitek Corporation. The Sondhi brand adhesive includes two lightly filled resin components that are mixed independently from each other and applied to the teeth and to the appliances respectively. The Unite brand adhesive, on the other hand, includes a mixed resin component and a mixed paste component; the resin component is first applied to both the teeth and the appliances, and then the paste component is applied to the appliances to form a so-called "sandwich" configuration. Another suitable two-component adhesive is Concise brand adhesive, also from 3M Unitek Corporation. The Concise brand adhesive includes a mixed paste component along with a mixed resin component that are placed on the appliances and teeth respectively. Alternatively, a resin-modified glass ionomer cement may be applied. Glass ionomer cements provide an additional advantage in that a separate tooth etching step is unnecessary.

Optionally, the bases 22 may be precoated with an orthodontic adhesive by the manufacturer as described in U.S. Pat. No. 7,137,812. Optionally, the precoated adhesive may have multiple layers and/or be patterned, as described in U.S. Pat. No. 7,374,420. As an additional option, the adhesive 31 may vary from one appliance 20 to the other as described in Published U.S. Patent Application No. 2005/0133384-A1.

The appliances 20 extend along a curved path 32 that is represented by the dashed line in FIG. 1. The path 32 may or may not extend in a reference plane parallel to the patient's occlusal plane depending on the practitioner's preferred treatment technique. For example, if the practitioner employs the "straight wire" technique, the path 32 of the appliances 20 may lie in a common place at the conclusion of treatment but typically will not lie in a common plane at the beginning of treatment.

The apparatus 10 also includes at least one elongated groove 34 that extends along the base of at least one appliance 20. In the illustrated embodiment, the apparatus 10 includes a number of grooves 34, each extending along the base of a corresponding one of the appliances 20. Each groove 34 provides a space between the inner wall sections of the matrix material 18 and the patient's tooth structure when the tray 12 is received on the patient's dental arch.

Each groove 34 extends along at least 25% and more preferably along at least 50% of the periphery of the base of the respective appliance 20. Most preferably, each groove 34 surrounds the base of the respective appliance 20. Preferably, the groove 34 is directly adjacent the base 22. However, as an alternative, the groove 34 may be slightly spaced away from the base 22 such that a relatively thin wall section of the matrix material 18 contacts the tooth in an area between the groove 34 and the appliance 20.

The overall configuration of an exemplary groove 34 is illustrated in FIG. 3 in elevational view. In this embodiment, the overall shape of the groove 34 is somewhat rectangular with rounded corners and slightly larger than the overall, somewhat rectangular shape (with rounded corners) of the base 22 (in FIG. 3, base 22 lies behind the adhesive 31). As an alternative, both the groove 34 and the base 22 may have matching shapes in elevational view resembling an ovoid. As yet another alternative, the overall shape of the groove 34 may be different than the overall shape of the base 22. As one example of the latter construction, the overall shape of the base 22 in elevational view may be somewhat rectangular or square while the overall shape of the surrounding groove 34 may be somewhat ovoid in elevational view.

Suitable methods for making the tray 12 are described in U.S. Pat. Nos. 7,020,963, 7,188,421, and 7,556,496. Preferably, the tray 12 also includes occlusal stops such as described in U.S. Pat. No. 7,556,496.

As one option to make the apparatus 10, the appliances 20 may be placed on a dental model as described in the preceding patent applications, and a quantity of material may then be deposited on the model in areas along the entire periphery of each appliance base 22. For example, a ring of material may be applied to the model in surrounding relation to the base 22 of each appliance 20. An example of a suitable material is dental restorative material such as Filtek Flow brand restorative material from 3M ESPE. Preferably, the material does not bond to the matrix material 18 as the latter is cured.

After the ring of material is applied to the dental model, the shell 16 is constructed as described in the preceding patent applications by placing spacer material over the dental model including the appliances 20 and the ring of material next to the base 22 of each appliance 20. After the shell 16 is formed, the shell 16 is removed from its position over the dental model and the spacer material is then detached from the dental arch model. Next, the outer shell 16 is placed over the dental model and uncured matrix material 18 is then added to the space between the shell 16 and the model. The matrix material 18 surrounds the appliance 20 and extends across and contacts its mesial, distal, occlusal, gingival and facial sides except in areas occupied by the ring of material.

After the matrix material 18 has been allowed to cure, the tray 12 is removed from the dental arch model along with the appliances 20. The rings of material previously applied to the model next to the appliances 20 remain with the model. The inner wall sections of the matrix material 18 have indentations next to the appliances 20 that resemble a negative image of the rings of material that protrude from the surface of the model teeth.

As an alternative method of making the apparatus 10, a stereolithography machine may be used to form a model of the dental arch showing the patient's teeth in their original, maloccluded positions. At the same time, the stereolithography machine forms rings of material surrounding the designated locations where the bases of the appliances 20 are to be placed. In this instance, the rings carried by the model teeth are used as guides for placement of the appliances as described in applicant's Published U.S. Patent Application No. 2006/0257821. However, as opposed to the method described in that patent application, the rings of material or placement guides are left in place on the dental arch model after the appliances 20 have been received on the model such that the placement guides form ringed indentations in the matrix material 18 of the tray 12.

FIG. 4 is an illustration showing an exemplary use of the apparatus 10 during an orthodontic bonding procedure. As shown, the tray 12 is placed over a dental arch 54, causing the base 22 of the appliance 20 to contact the enamel surface of the patient's tooth 56. When the tray 12 is positioned in this manner, the groove 34 provides a space between the patient's tooth surface and the inner wall section of the matrix material 18 facing the channel 14 and adjacent the appliance 20.

The space presented by the groove 34 provides a break between the close-fitting inner surface of the matrix material 18 and the matching outer surface of the patient's tooth 56. It is believed that this break functions to help reduce the effects of capillary action and/or surface tension and consequently hinder the migration of moisture in directions toward the adhesive 31.

After the adhesive 31 has cured, the apparatus 10 is removed from the patient's dental arch. Preferably, the shell 16 is first separated from the matrix material 18, which remains in place over the dental arch 54 along with the appliances 20. Next, the matrix material 18 is detached from the appliances 20. A hand instrument such as a scaler may be used to help hold each appliance 20 against the surface of the respective tooth 56 as the matrix material 18 is peeled away from the appliances 20. However, in instances where a relatively soft matrix material is employed or otherwise readily releases from the appliances 20, the use of a scaler to help avoid fracturing the fresh adhesive bond is optional.

Figure 5:
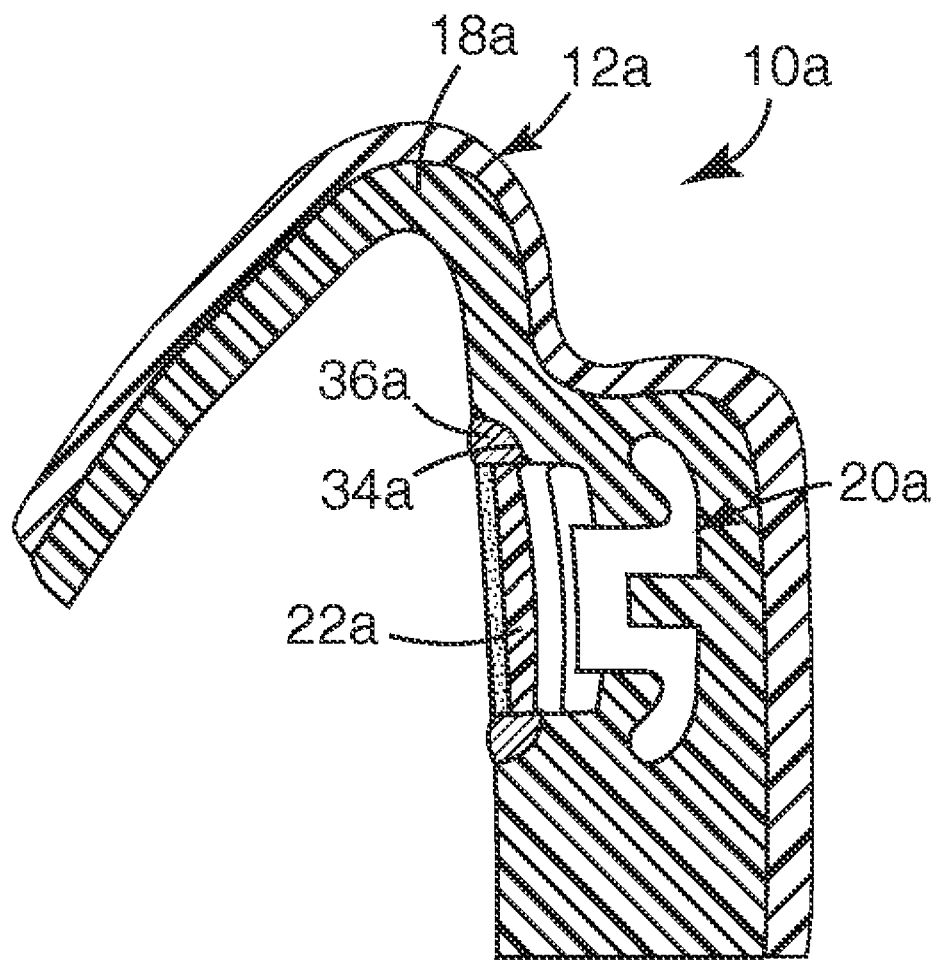
FIG. 5 is a view somewhat similar to FIG. 2 but showing an orthodontic indirect bonding apparatus according to another embodiment of the invention.

An apparatus 10a according to another embodiment of the invention is illustrated in FIG. 5. Except as set out in the paragraphs that follow, the apparatus 10a is substantially the same as the apparatus 10 described above and consequently a description of the similar aspects need not be repeated.

The apparatus 10a includes a tray 12a with a groove 34a that is similar to the groove 34. The groove 34a provides a space between the base 22a of the appliance 20a and adjacent inner wall sections of matrix material 18a. However, in this embodiment the groove 34a receives a quantity of absorbent material 36a for absorbing oral fluids. Examples of suitable absorbent materials 36a include nonwoven materials, solid inorganic oxides that react with water to form the corresponding hydroxides, particularly those of elements in Groups 1-2 and 13-17 of the Periodic Table such as calcium oxide, zeolites that may or may not be in the form of finely divided powders, and cellulose (such as cotton). Preferably, the absorbent material 36a is encapsulated to facilitate retention of the absorbed fluids and covered with a section of film that is permeable to oral fluids.

As another option, the absorbent material 36a may comprise super-absorbent sodium polyacrylate granules that are optionally placed within an absorbent hydrophilic fiber fill. Preferably, the sodium polyacrylate granules and fiber fill are contained within a film that is preferably permeable to oral fluids. The sodium polyacrylate granules may be made in a manner similar to the manufacture of polyacrylate granules that are used in disposable diapers.

Optionally, the absorbent material 36a may be covered by a flexible film layer that is made of a moisture permeable hydrophobic material. Such material feels dry to the touch and is somewhat similar to the material used in disposable diapers. Preferably, the absorbent material protrudes outwardly from adjacent wall sections of the matrix material 18a so that is firmly contacts the patient's tooth structure as the tray 12a is placed over the patient's dental arch. The absorbent material 36a, including any outer coverings or layers, is readily deformable to conform to the shape of the patient's tooth and to avoid hindering placement of the apparatus 10a over the patient's dental arch.

All of the patents and patent applications mentioned above are hereby incorporated by reference. The foregoing description is intended to exemplify various aspects of the invention and variations are possible. Consequently, the invention should not be deemed limited to the presently preferred embodiments described in detail above, but instead only by a fair scope of the claims that follow and their equivalents.

The invention claimed is:

1. A method for making an orthodontic indirect bonding tray assembly comprising:
   providing a model of a dental arch, wherein the model includes a number of model teeth, wherein at least one tooth includes a location that is designated to receive the base of an orthodontic appliance, and wherein the at least one tooth carries a quantity of material that protrudes from the surface of the tooth in an area next to the designated location;
   placing the base of an orthodontic appliance in the designated location;
   forming a tray that includes wall sections proximate an orthodontic appliance over the model and the orthodontic appliance, wherein the act of forming the tray is carried out by contacting the tray with the quantity of material that protrudes from the surface of the tooth in order to create at least one indentation in wall sections of the tray next to the appliance; and
   placing a quantity of absorbent material in the at least one indentation of the tray.

2. A method according to claim 1 wherein the quantity of material carried by the at least one tooth is sufficient to create an indentation that extends along at least 50% of the periphery of the base of the appliance.

3. A method according to claim 1 wherein the quantity of material carried by the at least one tooth is sufficient to create an indentation that extends along substantially the entire periphery of the base of the appliance.

4. A method according to claim 1 wherein the act of providing a model of the dental arch includes the acts of forming the at least one tooth and forming the quantity of material carried by the at least one tooth at the same time.

5. A method according to claim 4 wherein the acts of forming the at least one tooth and forming the quantity of material carried by the at least one tooth at the same time are carried out by rapid prototyping.

6. A method according to claim 1 wherein the act of providing a model of the dental arch includes the act of applying the quantity of material carried by the at least one tooth on the tooth.

7. A method according to claim 1 wherein the act of placing the base of the appliance in the designated location is carried out in part by using the quantity of material carried by at least one tooth as a guide.

8. A method according to claim 1 and including the act of placing the appliance in the tray.

9. A method according to claim 8 and including the act of placing a quantity of orthodontic adhesive on the base of the appliance after the appliance has been placed in the tray.

10. A method according to claim 1, wherein forming a tray over the model and the orthodontic appliance further comprises creating an indentation in a wall section of the tray spaced from the base of the appliance.

* * * * *

UNITED STATES PATENT AND TRADEMARK OFFICE
CERTIFICATE OF CORRECTION

| | | |
|---|---|---|
| PATENT NO. | : 8,114,327 B2 | Page 1 of 1 |
| APPLICATION NO. | : 12/566221 | |
| DATED | : February 14, 2012 | |
| INVENTOR(S) | : David K. Cinader, Jr. | |

It is certified that error appears in the above-identified patent and that said Letters Patent is hereby corrected as shown below:

ON THE TITLE PAGE:

ITEM (73) ASSIGNEE:

Delete "Innovation" and insert -- Innovative --, therefor.

Signed and Sealed this
Twenty-sixth Day of June, 2012

David J. Kappos
*Director of the United States Patent and Trademark Office*